United States Patent [19]

Takekawa

[11] Patent Number: 5,017,341
[45] Date of Patent: May 21, 1991

[54] AGGLUTINATION ANALYZING VESSEL

[75] Inventor: Hiroshi Takekawa, Sagamihara, Japan

[73] Assignee: Olympus Optical Co., LTD., Tokyo, Japan

[21] Appl. No.: 338,151

[22] Filed: Apr. 14, 1989

[30] Foreign Application Priority Data

Apr. 19, 1988 [JP] Japan ................................ 63-94674

[51] Int. Cl.⁵ .............................................. B01C 3/02
[52] U.S. Cl. ...................................... 422/102; 422/58; 422/73; 422/101; 436/165; 436/809; 435/299; 435/300; 435/301; 356/244; 356/246
[58] Field of Search ................... 422/102, 101, 58, 73; 436/165, 809; 435/284, 287, 299–301; 356/244, 246

[56] References Cited

U.S. PATENT DOCUMENTS

| | | | |
|---|---|---|---|
| 3,915,647 | 10/1975 | Wright | 435/299 |
| 4,154,795 | 5/1979 | Thorne | 422/102 X |
| 4,303,616 | 12/1981 | Kano et al. | 422/102 |
| 4,466,740 | 8/1984 | Kano et al. | 422/73 X |
| 4,678,757 | 7/1987 | Rapkin et al. | 422/101 X |
| 4,770,855 | 9/1988 | Sakuma | 422/73 X |
| 4,847,199 | 7/1989 | Snyder et al. | 422/73 X |
| 4,912,034 | 3/1990 | Kalra et al. | 422/58 X |

*Primary Examiner*—Robert J. Warden
*Assistant Examiner*—Lynn M. Kummert
*Attorney, Agent, or Firm*—Parkhurst, Wendel & Rossi

[57] ABSTRACT

An agglutination analyzing vessel for use in an immunological agglutination reaction in which there is provided a liquid-absorbable member made of porous material in at least a portion of an inclined bottom surface of a well provided in the analyzing vessel. A solution for a test liquid is absorbed into the liquid-absorbable member to cause a liquid flow directed downwardly in the test liquid. This downward liquid flow promotes the sedimentation of particles. Thus, both agglutination and non-agglutination particle patterns can be formed on the bottom surface of the vessel within a short time period.

11 Claims, 5 Drawing Sheets

FIG_1A
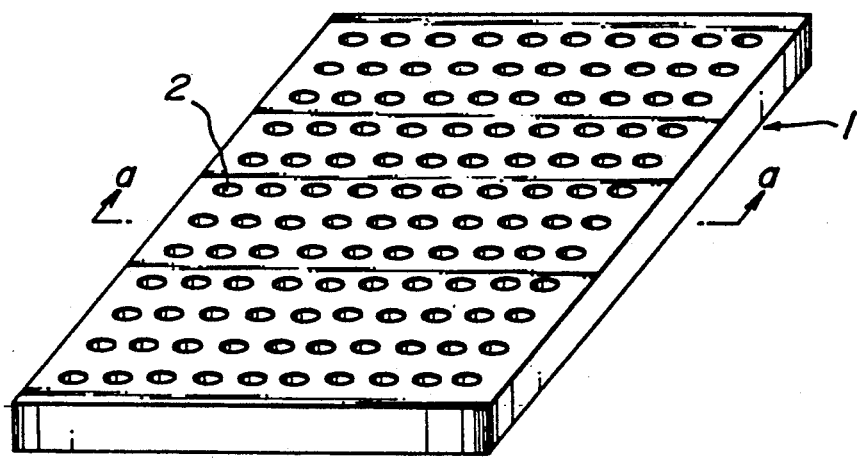
FIG_1B
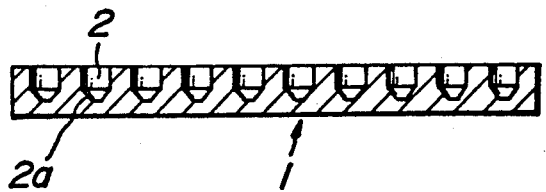

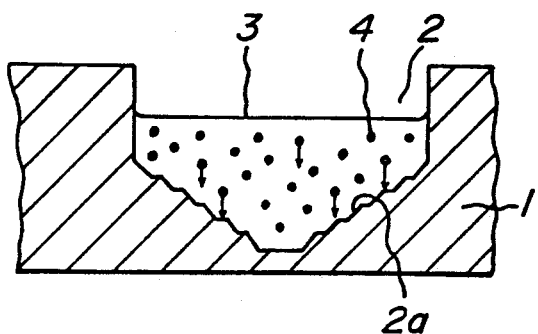
FIG_2A
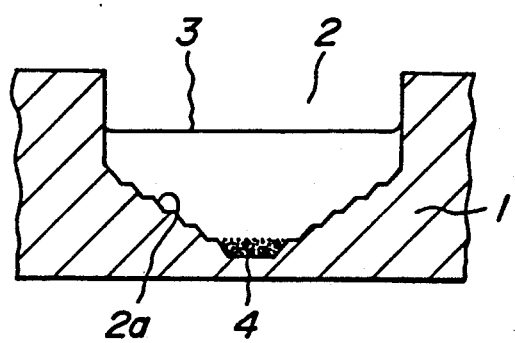
FIG_2D
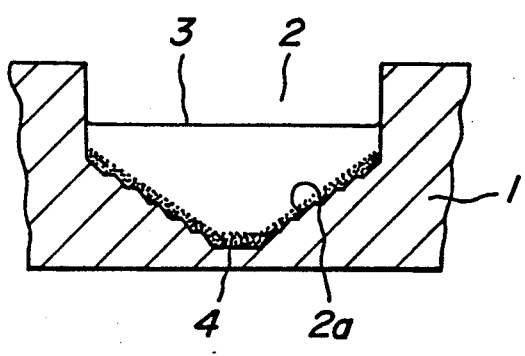
FIG_2B
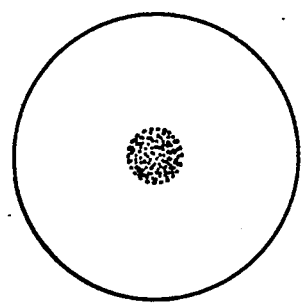
FIG_2E
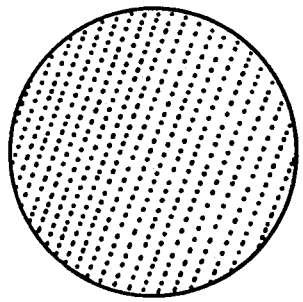
FIG_2C

AGGLUTINATION ANALYZING VESSEL

BACKGROUND OF THE INVENTION

Field of the Invention and Related Art Statement

This invention relates to an agglutination analyzing vessel for analyzing samples by means of agglutination patterns produced in the vessel due to immunological agglutination reactions, and more particularly to a vessel for identifying various kinds of blood types with the aid of agglutination patterns of blood corpuscles or for detecting various kinds of antibodies and antigens in sample solutions (like viruses, proteins or the like) with the aid of agglutination patterns of not only blood corpuscles but also particles of insoluble materials such as latex, carbon or the like.

The conventional agglutination analyzing vessels for identifying the blood types or detecting the antibodies and antigens in sample solutions with the aid of the immunological agglutination reaction patterns have been made of solid material such as plastics and glass as stated in U.S. Pat. No. 4,303,616. FIG. 1A is a perspective view showing a microplate 1 made of plastics, in which there are arranged in a matrix matter a number of wells 2, each having a conical base surface 2a, and FIG. 1B is a cross sectional view cut along line a—a of FIG. 1A. FIGS. 2A~2E are schematic views showing in an enlarged scale a process of the immunological agglutination reaction effected in one of the wells 2 provided in the microplate 1. It should be noted that a plurality of fine engravings or steps are regularly formed in the inclined base surface 2a of the well 2 in order to form a stable substrate layer of particles which are uniformly deposited on the inclined base surface 2a of the well 2.

In order to detect and measure the HBs antigen in a test blood, there has been proposed a method stated as follows. As shown in FIG. 2A, a reagent solution 3 including particles 4, on which anti HBs antibodies have been bound, (for example, red blood cells of animals), and sample serum are introduced into the well 2 of the microplate 1 to form a test liquid which is then set in a stationary state. Thereafter, the particles 4 in the reagent solution 3 start to settle down in the analyzing vessel gradually and slowly to form an agglutination pattern or a non-agglutination pattern on the inclined bottom surface 2a of the well 2.

In the case of when the sample serum includes the HBs antigen, an antigen-antibody reaction is effected in the test liquid introduced in the well 2 not only when the particles 4 fall down in the solution 3 but also after the particles 4 have been settled on the inclined bottom surface 2a of the well 2. The particles 4 are agglutinated with each other and are deposited so as to be spread uniformly all over the inclined bottom surface 2a of the well 2 to form an agglutination pattern. FIG. 2B is a cross sectional view showing the well in which the agglutination pattern is formed on the inclined bottom surface 2a and FIG. 2C is a schematic plan view of the pattern viewed from the above.

In the case of when the sample serum does not include the HBs antigen, the particles 4 settling on the inclined bottom 2a of the well 2 roll down along the inclined bottom surface 2a of the well 2, since no antigen-antibody reaction has occurred in the test liquid. Thus, the particles 4 are collected at the lowest portion of the bottom surface 2a and a non-agglutination pattern as shown in FIG. 2D is formed thereon. FIG. 2E is a schematic plan view of the non-agglutination pattern viewed from above. In such a manner, the HBs antigen existing in the sample blood is detected by the difference of the particle patterns formed on the bottom surface 2a of the well 2.

However, in this method, since the particle pattern is formed with the aid of the natural sedimentation of the particles 4, in which the particle pattern is formed only depending on the specific gravity and temperature of the sample solution and the weight and dimension of the particle, it takes one or two hours until clear particle patterns are formed on the inclined bottom surface 2a of the well 2. Thus, the test cannot be conducted speedily.

Another known method for detecting and measuring the HBs antigen is to centrifuge the microplate containing a mixture of reagent particle solution and the sample serum therein. In this method, the sedimentation speed of the particles 4 contained in the test liquid is promoted by the centrifugal force.

According to this method, it is possible to promote the sedimentation speed of the particles in the test liquid but a bucket is necessary to set the microplate in the centrifuge, and further the centrifuge operation is not very easy. Thus, the test cannot be easily conducted.

SUMMARY OF THE INVENTION

In order to solve the problem mentioned above, the present invention has for its object to provide an agglutination analyzing vessel which can promote the sedimentation speed of the particles in the test solution. Therefore, the time for forming the discernable particle pattern on the bottom surface of the vessel can be shortened, and the agglutination analyzing can be conducted within a short time.

In order to attain the above object, the agglutination analyzing vessel according to the invention comprises:
a main body made of solid material;
a well formed in the main body and having a bottom surface, at least a part of which is inclined; and
a liquid-absorbable member formed in at least a portion of the bottom surface of the well; and whereby a solution of a test liquid introduced in the reaction vessel is absorbed in the liquid-absorbable member to cause a liquid flow directed downwardly in the test liquid to promote a sedimentation of particles contained in the test liquid.

According to the invention, the solution of the test liquid contained in the analyzing vessel is absorbed into the liquid-absorbable member, which is formed in at least a part of the bottom of the analyzing vessel. Thus, since the particles in the solution are subjected to a downward force by the liquid flow, which is caused when the solution is absorbed in the liquid-absorbable member, in addition to the natural sedimentation, the sedimentation of the particles is promoted and the time for forming the particle pattern on the bottom surface of the well can be shortened. It should be noted that the liquid flow is not so strong that the particle pattern formed on the inclined bottom surface of the reaction vessel is affected thereby.

BRIEF DESCRIPTION OF THE DRAWINGS

FIG. 1A is a perspective view showing the known microplate having a plurality of analyzing vessels for use in agglutination analyzing of the test serum and FIG. 1B is a cross-sectional view of the microplate cut along line a—a of FIG. 1A;

FIGS. 2A to 2E are schematic views depicting the process that agglutination pattern or non-agglutination pattern is formed on the inclined bottom surface of the agglutination analyzing vessel;

DETAILED DESCRIPTION OF THE PREFERRED EMBODIMENTS

Figure 3:
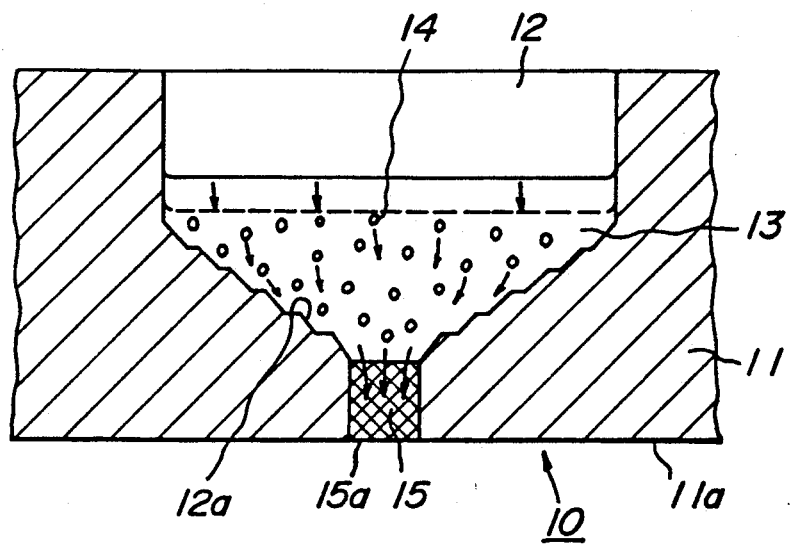
FIGS. 3 to 5 are cross-sectional views illustrating first to third embodiments of the agglutination analyzing vessel having a conical bottom surface according to the present invention, respectively.

FIG. 3 is a cross-sectional view showing the first embodiment of the agglutination analyzing vessel according to the invention. A well 12 provided in a microplate body 11, made of solid material which does not absorb a liquid, has a conical bottom surface 12a. There are regularly provided a plurality of engravings in the inclined bottom surface 12a in order to uniformly deposit and hold particles 14 settled thereon. A liquid-absorbable member 15 is formed in the lowest portion of the inclined bottom surface 12a so as to be extended to the bottom surface of the microplate body 11. When a test liquid, including particles on which anti HBs antibodies are bound, and a sample solution are introduced into the thus structured analyzing vessel 10 and are set stationarily, the solution 13 is gradually absorbed into the liquid-absorbable member 15. In the test liquid a liquid flow is created downwardly by the absorption of the solution 13 into the liquid-absorbable member 15, as shown by arrows in FIG. 3. In this case, since a force caused by the liquid flow effects the promotion of the sedimentation of the particles 14 in the test liquid in addition to the gravity of the particles per se, the sedimentation speed of the particles 14 increases. Generally, the antigen-antibody reaction is generated as soon as the antigen is bound with the antibody. Therefore, as the sedimentation speed of the particles 14 is made faster, the agglutination pattern is formed on the bottom surface 12a of the well 12 within a short time period. As above, when in case the particles 14 are not agglutinated with each other, the non-agglutination pattern is also speedily formed on the bottom surface of the vessel 12.

The absorbing speed of the liquid absorbable member 15 can be selected in accordance with the reaction speed of the antigen-antibody reaction in the test liquid by selecting the material of the liquid-absorbable member or by modifying the porosity of the liquid-absorbable member.

In this embodiment, since the liquid-absorbable member 15 is formed in the bottom surface 12a of the well 12 so as to be extended to the bottom surface of the microplate body 11, the solution absorbed in the liquid-absorbable member 15 is vaporized from the lower surface 15a thereof into the outer space. Therefore, the liquid flow formed in the test liquid is continued as long as the solution 13 is exists in the well 12. Thus, the downward liquid flow in the test liquid can be continued for a long time, so that the precise agglutination pattern can be formed on the bottom surface 12a of the well 12 even when the particles have a weak agglutination force.

Figure 4:
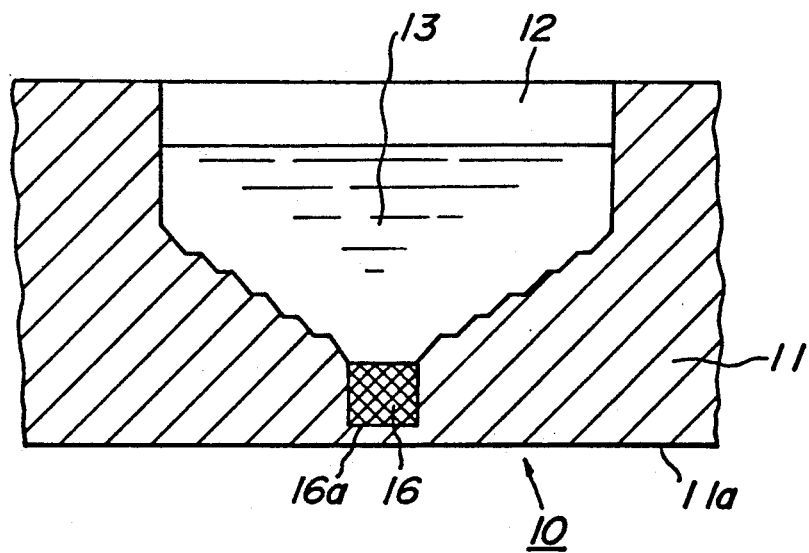

FIG. 4 is a cross-sectional view illustrating the second embodiment of the agglutination analyzing vessel according to the invention. In this embodiment, the agglutination analyzing vessel 10 has the same construction as that of the first embodiment but a liquid-absorbable member 16 is not extended to the bottom surface 11a of the microplate body 11. Since the lower surface 16a is not exposed to the bottom surface of the microplate body, a time period during which the liquid flow is generated in the well 12 depends upon the liquid holding capacity of the liquid-absorbable member 16. However, in such structure, since the solution 13 is never dropped from the liquid-absorbable member 16 to the outside of the microplate 11, contamination of the analyzing operators or the automatic analyzing apparatus for analyzing the agglutination pattern formed in the analyzing vessel 10 is prevented.

Figure 5:
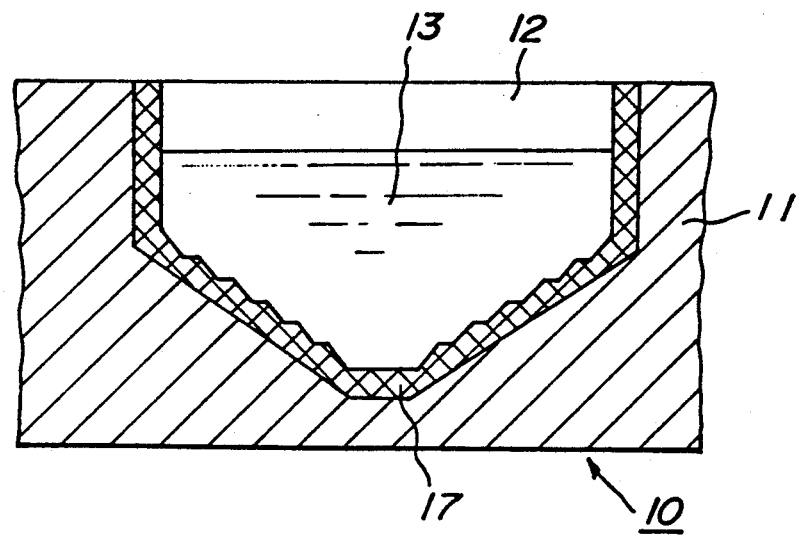

FIG. 5 is a cross-sectional view depicting the third embodiment of the agglutination analyzing vessel having a conical bottom surface according to the invention. In this embodiment, in all over the inner surface of the well 12 of the analyzing vessel 10 is formed a liquid-absorbable member 17 with a substantially uniform thickness. In this embodiment, the solution 13 is absorbed into the liquid-absorbable member 17 at a wider range; and thus larger liquid flow is generated in the well 12. Thus, the larger liquid flow forms the particle pattern on the bottom surface 12a of the well 12 more precisely and speedily. In addition to this, since the lower surface of the liquid absorbable member 17 is not exposed in the bottom surface of the microplate body 11, there is no problem of contamination. In the surface of the liquid-absorbable member are formed fine steps.

Figure 6:
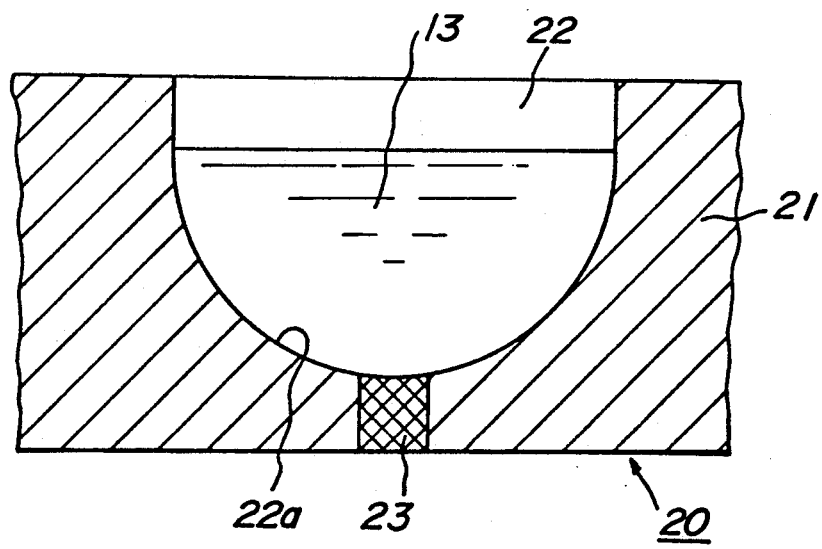
FIGS. 6 to 8 are cross-sectional views illustrating fourth to sixth embodiments of the agglutination analyzing vessel having a winecup-shaped bottom surface according to the present invention, respectively.
Figure 7:
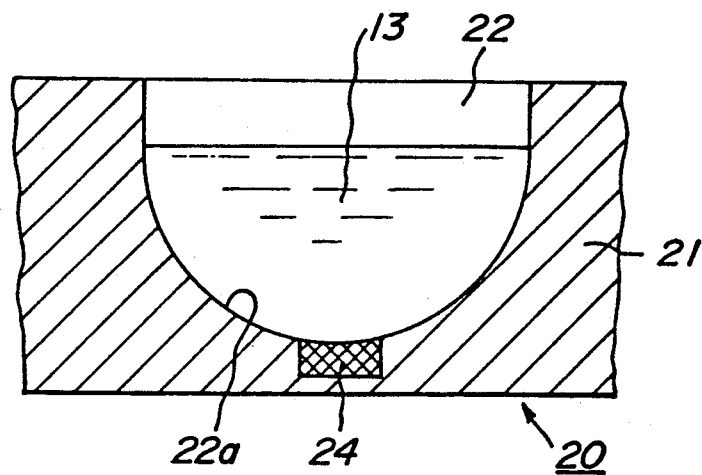
Figure 8:
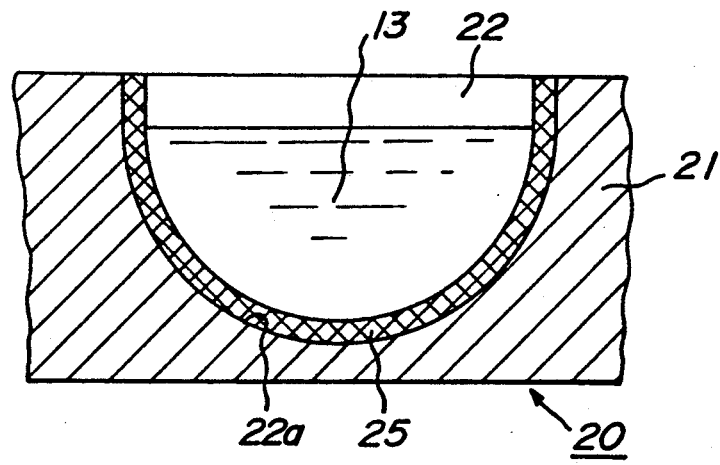

FIGS. 6 to 8 are cross-sectional views representing the fourth to sixth embodiments of the agglutination analyzing vessel according to the invention, respectively. In these embodiments, the well 22 formed in the vessel 20 has a winecup-shaped bottom surface 22a and the arrangement of the liquid-absorbable members 23 25 are corresponding to that of the liquid-absorbable members 15~17 of the first to third embodiments. Such analyzing vessels having a winecup-shaped bottom surface can be manufactured easily and are suitable for identifying the ABO blood type pattern in which the agglutination is effected more strongly.

According to the invention, natural and synthetic material such as pumice, sponge and paper can be used for the liquid-absorbable member. When the particle pattern formed in the analyzing vessel is detected photoelectrically with the aid of light transmitting through the vessel, the liquid-absorbable member has to be made of high permeable material such as a bundle of fine glass fibers having narrow spaces between adjacent fibers.

As stated above, according to the invention it is possible to promote the sedimentation of the particles contained in the test liquid by arranging the liquid-absorbable member in at least one portion of the bottom surface of the well provided in the analyzing vessel. Thus, the agglutination and non-agglutination particle patterns can be formed in the agglutination analyzing vessel within a short time, so that the test result can be obtained speedily.

What is claimed is:

1. An agglutination analyzing vessel for analyzing a solution of particles in a test liquid for the presence of an agglutination reaction, comprising:

a main body made of solid material;
   a well formed in said main body and having a bottom surface, at least part of said bottom surface of said well being inclined; and means for absorbing and retaining the solution therein, said absorbing and retaining means being formed on the entirety of said bottom surface of said well;

whereby the solution is absorbed in said absorbing and retaining means when introduced into said well, said absorbing and retaining means causing a downward flow of the test liquid which promotes sedimentation of the particles in the test liquid.

2. The agglutination analyzing vessel of claim 1, wherein said absorbing and retaining means consists of paper.

3. The agglutination analyzing vessel of claim 1, wherein said absorbing and retaining means consists of pumice.

4. The agglutination analyzing vessel of claim 1, wherein said absorbing and retaining means consists of a sponge.

5. The agglutination analyzing vessel of claim 1, wherein said absorbing and retaining means is made of a bundle of fine glass fibers having narrow spaces between adjacent glass fibers.

6. The agglutination analyzing vessel of claim 1, wherein said at least part of said bottom surface of said well has a conical shape, said absorbing and retaining means also being formed in a central portion of the conical-shaped part of said bottom surface of said well so as to extend to a bottom surface of said main body.

7. The agglutination analyzing vessel of claim 1, wherein said at least part of said bottom surface of said well has a conical shape, said absorbing and retaining means also being formed in a central portion of the conical-shaped part of said bottom surface of said well and partially extending towards a bottom surface of said main body.

8. The agglutination analyzing vessel of claim 1, wherein said at least part of said bottom surface of said well has a conical shape.

9. The agglutination analyzing vessel of claim 1, wherein the at least part of said bottom surface of said well has a winecup-shape, said absorbing and retaining means also being formed in a central portion of said winecup-shaped part of said bottom surface of said well so as to extend to a bottom surface of said main body.

10. The agglutination analyzing vessel of claim 1, wherein the at least part of said bottom surface of said well has a winecup-shape, said absorbing and retaining means also being formed in a central portion of said winecup-shaped part of said bottom surface of said well and partially extending towards a bottom surface of said main body.

11. The agglutination analyzing vessel of claim 1, wherein the at least part of said bottom surface of said well has a winecup-shape.

* * * * *